US00PP11011P

United States Patent [19]

Fleming et al.

[11] Patent Number: Plant 11,011

[45] Date of Patent: Jul. 20, 1999

[54] HIBISCUS PLANT NAMED 'ROYAL GEMS'

[76] Inventors: David W. Fleming; James R. Fleming, both of 8101 S. 14th St., Lincoln, Nebr. 68512

[21] Appl. No.: 08/962,866

[22] Filed: Nov. 3, 1997

[51] Int. Cl.[6] ..... A01H 5/00

[52] U.S. Cl. ..... Plt./67.8

[58] Field of Search ..... Plt./67.8

*Primary Examiner*—Howard J. Locker

[57] ABSTRACT

A new and distinct cultivar of winter hardy hibiscus plant named 'Royal Gems' is the result of a unique hybridi zation. This new and distinct cultivar is characterized primarily as to novelty by its extreme cold hardiness to Zone 4, its dark purple undercurved ovate leaves, its v ery large luminescent pink flowers, its vigorous and uniform growth habit, and its floriferous nature from midsummer until frost.

4 Drawing Sheets

BACKGROUND OF THE NEW PLANT

The new plant of this invention is the result of a unique hybridization, with the breeding achievement being evidenced in the outstanding combination of characteristics exhibited by this new and distinct Hibiscus plant, which include:

(a) Refined foliage, characterized by the leaves being ovate and slightly underturned, with smooth margins and evenly distributed dark purple coloration which in combination gives a three dimensional effect to the foliage;
(b) Very large flowers that are outstanding for their thick texture and luminescent pink coloration;
(c) The plant being very floriferous with flowers that stay open one full day;
(d) The plant being medium-sized, but vigorous, with compact and uniform breaking action which gives it unique landscape utility; and
(e) The plant being so hardy it can conssistently withstand winter temperatures of at least −30 degrees Fahrenheit.

SUMMARY OF THE INVENTION

'Royal Gems' was the result of a 40 year breeding program. Its ancestry includes *Hibiscus moscheutos* and *Hibiscus coccineus.* More specifically, the plant resulted from 'Pink Perfection' (not patented), a Fleming hybrid of *Hibiscus moscheutos*, being crossed onto a selfed, unnamed reddish-purple leafed seedling, a Fleming hybrid of *Hibiscus coccineus.*

This new plant first bloomed in the summer of 1985 and was selected by David and James Fleming on their property in Lincoln, Nebr. Asexual propagation of the plant by cuttings and by root division in Lincoln, Nebr., has shown that the unique and distinguishing features of the plant are faithfully transmitted from generation to generation and appear to be firmly fixed.

Since its origin, the plant has bloomed from midsummer until frost, while exhibiting the above mentioned distinctive characteristics. This hardy hibiscus plant contributes to the market with its sheer beauty, its compact growth habit, it great resistance to disease and insects, its stability through extremes in rain and drought, and its extreme hardiness.

BRIEF DESCRIPTION OF THE DRAWINGS

The flower, bud, foliage, and growth habit of the plant are shown in the attached illustrations.

More specifically, Sheet 1 is a close up view of the flower.

Sheet 2 stems and blooms of the cultivar, showing bloom and foliage orientation and plant habit.

Sheet 3 shows buds in varying stages of maturity, and illustrated foliage coloration and veining.

Sheet 4 depicts immature buds and shows the foliage in greater detail. The colors illustrated are as true as is reasonably possible to attain in photographic illustrations of this type. The colors illustrated may be slightly off due to light reflectance.

DESCRIPTION OF THE NEW PLANT

What follows is a detailed description of the new cultivar. The specific color designations set forth by PLATE number designations are in accordance with the *Dictionary of Color* (Maerz and Paul), while general color recitations are consistent with ordinary American color terminology.

'Royal Gems' has not been observed under all possible environmental conditions. It is to be understood that the phenotype may vary significantly with variations in environment such as temperature, light intensity, and day length, without, however any diference in the genotype of the plant. The following botanical characteristics and observations are taken from the plant when grown under normal outdoor conditions in Lincoln, Nebr.

THE PLANT

Parentage:
- *Seed parent.*—Unnamed Fleming reddish-purple leafed seedling of *Hibiscus coccineus.*
- *Pollen parent.*—'Pink Perfection', a Fleming hybrid of *Hibiscus moscheutos.*

Origin: A selected seedling of from the stated cross.
Type of plant: Hardy; Herbaceous perennial.
Classification: Hybrid Hibiscus plant.
Propagation: Relatively easy to propagate; holds its distinguishing charateristics through successive propagations by cuttings and divisions.
Size: About 28–40 inches tall; about 24–30 inches wide.
Form: Symmetrical; annual growth from perennial roots.
Habit: Upright and uniformly branched.
Growth: Vigorous.
Hardiness: Hardy to at least −30 degrees Fahrenheit.
General health: Plant is very disease resistant; very pest resistant.
Propagation: Relatively easy; fast rooting.
Foliage: Ovate leaves with smooth margins that turn under slightly, leaves have dark purple coloration.
1. *Arrangement.*—Alternate.

2. *Shape.*—Juvenile — ovate, glabrous, flat. Mature — refined, ovate, margins smooth and slightly underturned.
3. *Size.*—Mature leaf — (petiole base to apex) length about 5 inches (13 cm), width about 3½ inches (9 cm).
4. *Color.*—Young leaves (upper side) — (Eggplant) H-12, page 119, PLATE 48; background green L-10, page 69, PLATE 23. Mature leaves (upper side) — (Mulberry) J-9, page 119, PLATE 48; background green J-1, page 71, PLATE 24. Veins — L-7, page 37, PLATE 7. Underside of leaves — H-2, page 69, PLATE 223.
5. *Surface texture.*—Glabrous (to very glabrous on young leaves).
6. *Petiole length.*—About 3½ inches (9 cm).
7. *Petiole color.*—L-7, page 37, PLATE 7.

Stems: The stems are stout at the base, becoming more slender toward the apices; coloration is consistent with the petiole.

THE FLOWER

Blooming period: Profuse from midsummer until frost.

Flower diameter: Very large; about 8½ inches (22 cm) to 11½ inches (29.5 cm).

Borne: Singly in leaf axils, from midpoint of stems upward.

Bloom duration: Individual bloom lasts one full day.

Form: Flat; petals very overlapping.

Bud:

1. *Length.*—About 2½ inches (5.6 cm).
2. *Color.*—K-6, page 31, PLATE 4.
3. *Duration.*—One to two weeks.

Corolla:

1. *Petal character and dimensions.*—Flat and very overlapping. Length is about 4½ inches (11.5 cm). Width is about 4½ inches (11.5 cm).
2. *Coloration.*—Luminescent pink bloom with red center or eye about 2 inches (5 cm) in diameter. (a). Pink petals — J-2, page 127, PLATE 52. (b). Venation in petals — L-6, page 31, PLATE 4. (c). Eye zone — L-6, page 31, PLATE 4 (inner), and K-6, page 33, PLATE 5 (outer).
3. *Texture.*—Smooth.
4. *Substance.*—Medium thick.
5. *Shape.*—Relatively flat and very overlapping.

Reproductive organs:

1. *Staminal column.*—Stamen along basal two-thirds. Stamen length — About 1½ inches (4 cm). Stamen color — I-3, page 25, PLATE 1. Pollen color — K-2, page 43, PLATE 10.
2. *Style.*—Terminates upper one-third of Staminal column. Stigmatic lobe color — H-6, page 37, PLATE 7.

Calyx: Connate at the base; about 1½ inches (3.5 cm) in length.

Stipules: None.

Epicalyx: Whorl of bracts.

1. *Shape.*—7–10 slender, sword-shaped bractlets.
2. *Length.*—About 1.2 inches (2.7 cm).
3. *Color.*—K-6, page 67 PLATE 22; tips L-8, page 37, PLATE 7.

Peduncle:

1. *Length.*—About 2½ to 3 inches (7–7.5 cm).
2. *Strength.*—Stiff and sturdy.

GENERAL OBSERVATIONS

This plant, as a hybridized hardy Hibiscus, is valuable to the landscape market for its improvements in very large thick-textured pink flowers, refined dark purple colored ovate leaves with smooth underturned margins, all around vigor, good breaking action, and adaptation to extreme environments, including the ability to consistently survive winter temperatures of at least −30 degrees Fahrenheit.

We claim:

1. A new and distinct cultivar of Hibiscus plant, as herein shown and described, characterized by its bold ovate dark purple foliage with smooth underturned margins, its very large pink flowers, its vigor, and its hardiness.

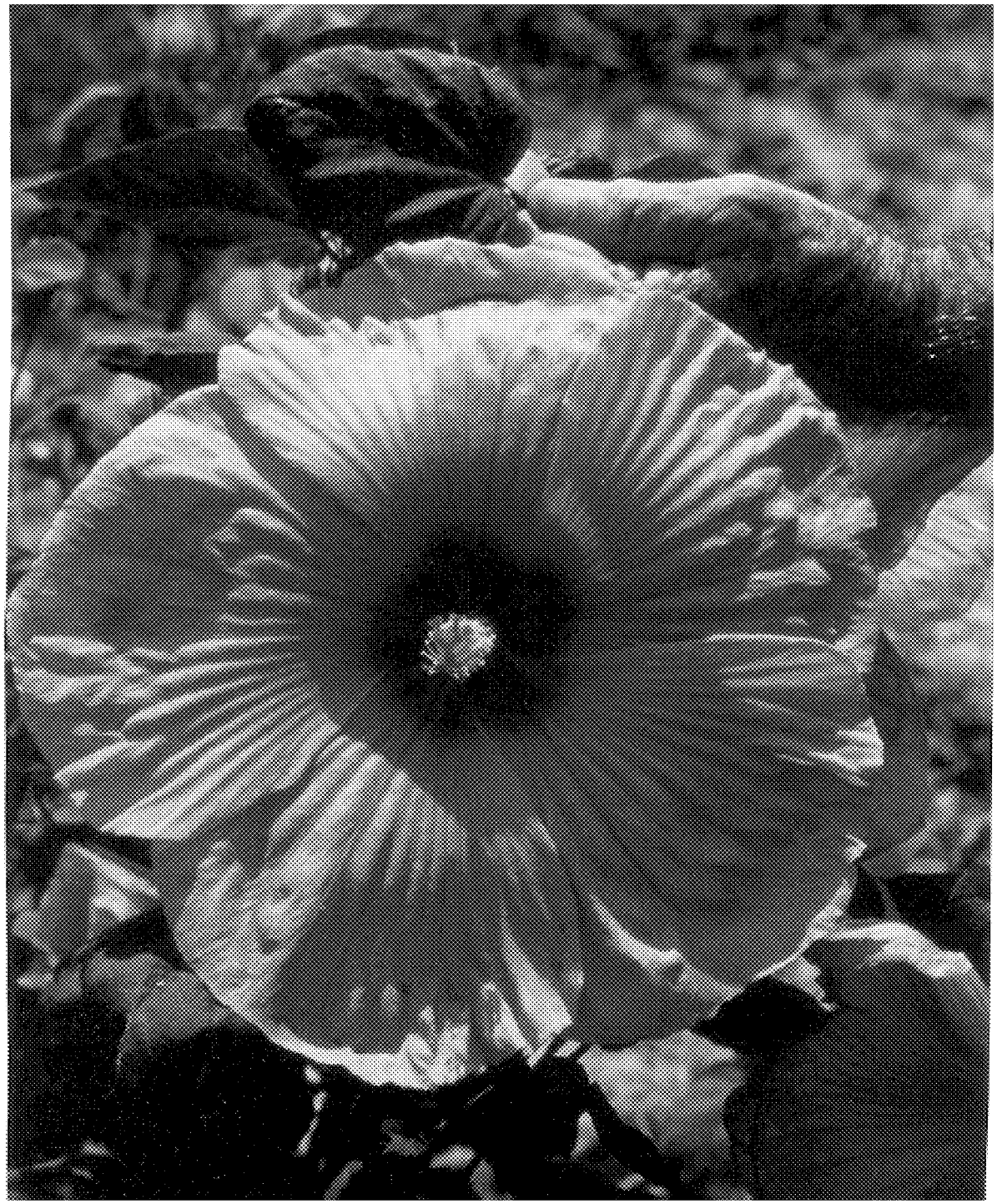

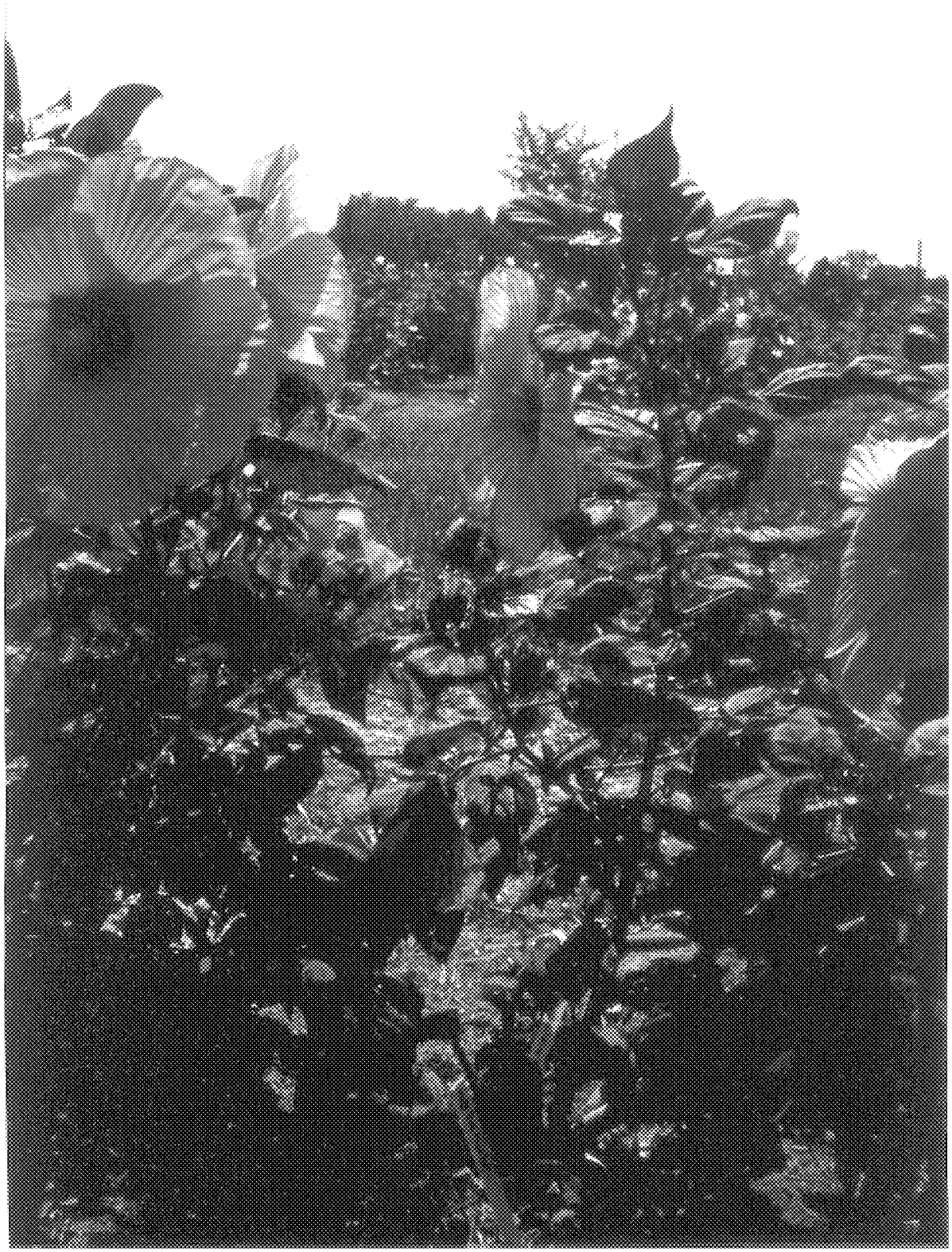

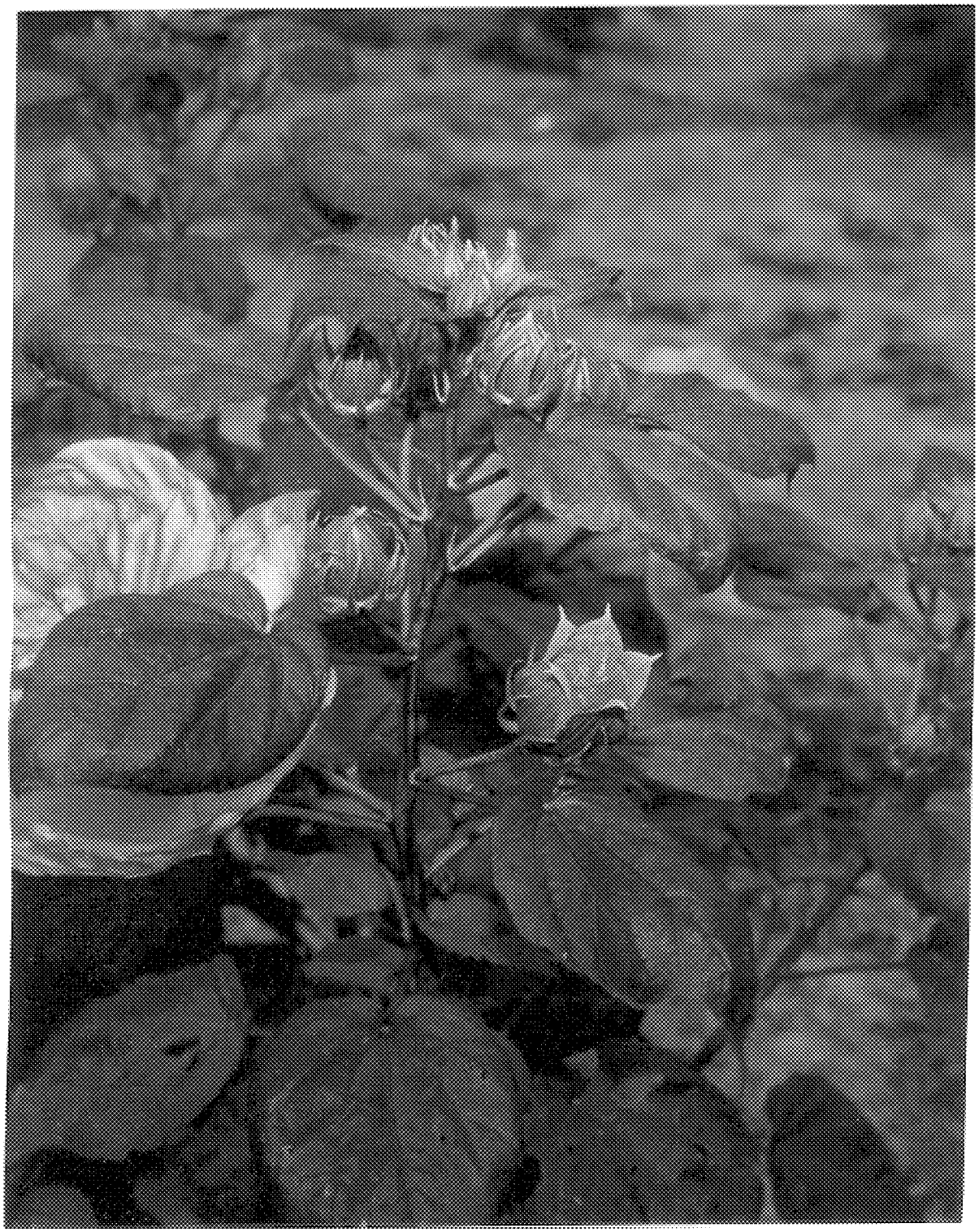

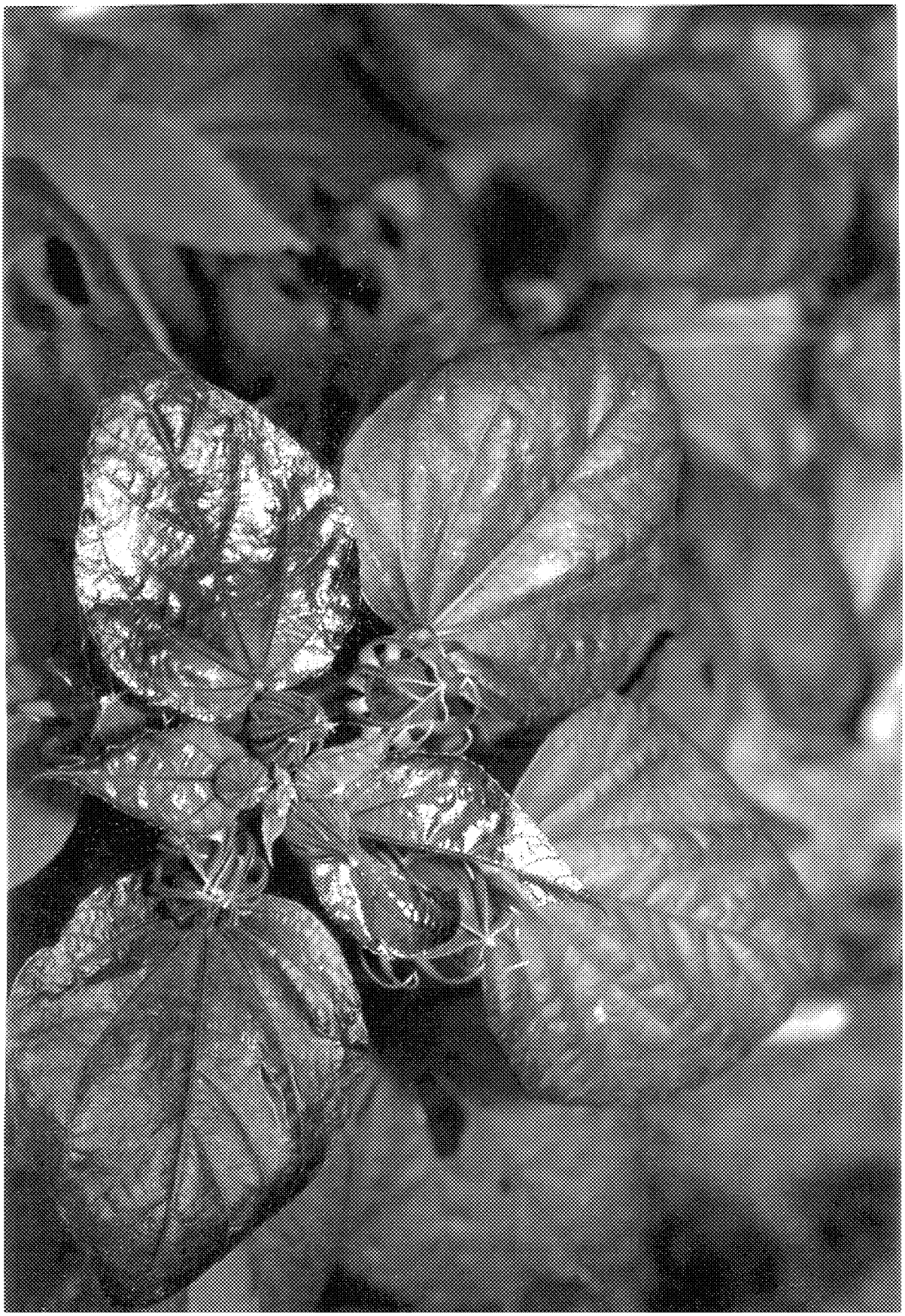

* * * * *